United States Patent [19]

McHugh

[11] Patent Number: 4,459,307
[45] Date of Patent: Jul. 10, 1984

[54] ANTIBACTERIAL DRUG

[76] Inventor: John E. McHugh, 16633 Ventura Blvd., Encino, Calif. 91436

[21] Appl. No.: 478,803

[22] Filed: Mar. 24, 1983

Related U.S. Application Data

[63] Continuation of Ser. No. 244,086, Mar. 16, 1981, abandoned.

[51] Int. Cl.³ .................. A61K 31/335; A61K 31/34; A61K 7/16
[52] U.S. Cl. .................................. 424/279; 424/285; 424/49
[58] Field of Search ............................... 424/279, 285

[56] References Cited

U.S. PATENT DOCUMENTS

| | | | |
|---|---|---|---|
| 3,991,211 | 11/1976 | Cebrian | 424/331 |
| 4,046,918 | 9/1977 | Cebrian | 424/331 |
| 4,046,919 | 9/1977 | Cebrian | 424/338 |
| 4,256,763 | 3/1981 | McHugh | 424/285 |

FOREIGN PATENT DOCUMENTS

| | | | |
|---|---|---|---|
| 0768704 | 12/1971 | Belgium | 424/279 |
| 2130346 | 12/1971 | Fed. Rep. of Germany | |
| 2,351,512 | 4/1975 | Fed. Rep. of Germany | |
| 1383293 | 2/1975 | United Kingdom | |

OTHER PUBLICATIONS

The Merck Index, 9th Ed., pp. 983–984, "7349".
Gilman et al., The Pharmacological Basis of Therapeutics, Sixth Edition, pp. 1086–1093 and 1100–1104.
The National Formulary, Fourteenth Edition, (NFXIV), pp. 563 and 564.
Chemical Abstracts, vol. 83:84879t, (1975).
Bauer, D. J., The Specific Treatment of Virous Diseases, University Park Press, 1977, pp. 50–57, pp. 71–85, 107, 109, 118, 122.
Melnick, J. L., Editor, Monographs in Virology, vol. 11, S. Karger, 1976: Becker, Y., Antiviral Drugs: Mode of Action and Chemotherapy of Viral Infections of Man, pp. 15, 57, 78, 84
MEDLARS, Offline Bibliographic Citation List, National Library of Medicine, National Interactive Retrieval Service, "Trifluorothymidine", Apr. 11, 1980, requested by John E. McHugh.
MEDLARS, Offline Bibliographic Citation List generated by National Library of Medicines, National Interactive Retrieval Service, "Effect of Antiviral Drugs on Herpes Simplex and Herpes Zoster", Apr. 16, 1981, requested by John E. McHugh.
Declaration of Douglas I. Hepler, filed in file wrapper of McHugh, Treatment of Herpes Simplex Infections and Acne, No. 4,256,763, Mar. 17, 1981.
Chapman, C. F., Editor, Human Diseases Caused by Viruses, Recent Developments, Oxford University Press, 1978, pp. 20, 161, 315, 318, 330, 335.
Fenner, F., and White, D. O., Medical Virology, 2d Edition, Academic Press, 1976, p. 148.
Hope-Simpson, R. E., The Nature of Herpes Zoster; A Long-Term Study and a New Hypothesis, Proceedings of The Royal Society of Medicine, 28:9–20, 1965.
Goodman & Gilman, Pharmacological Basis of Therapeutics, 4th Edition 1977, pp. 1021–1022.
Kaminester, L., Journal of the American Medical Association, 239:2171–72, May 19, 1978.
Chemical Abstracts 76: 103763z, (1972).
Weisz, Paul B., *The Science of Biology*, 3d ed., p. 240, (1967).
Villee, Claude A., *Biology*, 3d ed., p. 117, (1957).
Breed, Murray & Smith, Bergey's Manual of Determinative Bacteriology, Seventh Edition, Williams & Wilkins Co., 1957.
Barile & Razin, eds., The Mycoplasmas, vol. 1, Cell Biology, Academic Press, 1979, pp. xiii–xv, 24–41, 153, 169, 273–275, 482–483, 15–17.
Lennette, ed., Manual of Clinical Microbiology, Third Edition, American Society For Microbiology, 1980, pp. 83, 87–90, 128, 131–137, 195–197, 217, 293–294, 301–303, 306–307, 316–317, 365–370, 426, 431, 438, 440–441, 450, 498–499.
Nester et al., Microbiology, Second Edition, Holt, Rinehard & Winston, 1978, pp. 459–461.

*Primary Examiner*—Jerome D. Goldberg
*Assistant Examiner*—John M. Kilcoyne
*Attorney, Agent, or Firm*—Lyon & Lyon

[57] ABSTRACT

There is disclosed a method for treating and preventing infections caused by bacteria comprising the administration of effective dosage of 3,3-Bis(p-hydroxyphenyl)-phthalide (phenolthalein). The dosage may be administered orally or topically or by injection.

14 Claims, No Drawings

ANTIBACTERIAL DRUG

This is a continuation of application Ser. No. 244,086, filed Mar. 16, 1981, now abandoned.

BACKGROUND OF THE INVENTION

This invention relates to the discovery that 3,3-Bis(p-hydroxyphenyl)phthalide (hereafter phenolphthalein) is an effective treatment against certain bacterial conditions, diseases and symptoms.

Phenolphthalein has long been known as one of the group of primary diphenylmethane cathartics. The cathartic effect of phenolphthalein was reportedly discovered in 1902 and since that time it has been widely employed in laxative formulas. It is also reported that phenolphthalein is relatively nontoxic. Goodman & Gillman, *Pharmocological Basis of Therapeutics* (4th Edition 1977), pgs. 1021-22. Phenolpthalein is also used as an indicator in the titration of mineral and organic acids in most alkalis.

Applicant also disclosed methods and uses of phenolphthalein as an antiviral drug in TREATMENT OF HERPES SIMPLEX INFECTIONS AND ACNE, U.S. Pat. No. 4,256,763, filed Sept. 19, 1978, and issued Mar. 17, 1981.

There are estimated to be over 2,000 species of bacteria, although only a small portion are pathogenic. Weisz, Paul B., *The Science of Biology* (3d Ed. 1967), pg. 240; Villee, Claude, A., *Biology* (3d Ed. 1957), pg. 117 et seq. There are not many places which are devoid of bacteria. They are abundant in air, liquid such as milk, in and on the bodies of animals and plants both living and dead.

There are three general classifications of bacteria: bacilli (rod-like), cocci (spherical) and spiral forms. The spherical or cocci forms occur singly in some species, in groups of two, in long chains (streptococci) or in irregular clumps resembling bunches of grapes (staphylococci). Bacilli may occur as single rods or as long chains of rods joined together. The spiral forms are of two types: the spirilla, and the spirochetes.

The majority of bacteria utilize atmospheric oxygen in respiration; such forms are called aerobes. Other bacteria can grow and multiply in absence of free oxygen, getting their energy by the anaerobic metabolism of carbohydrates for amino acids and accummulating a variety of partially oxidized intermediates—alcohol, glycerol or lactic acid. Obligate anaerobes will grow only in the absence of oxygen—they are quickly killed by molecular oxygen. Facultative anaerobes will metabolize equally well in the presence or absence of oxygen. Villee at 119-121.

It is an object of the present invention to provide a fast acting, effective treatment of bacterial infections, whether topically or internally.

It is a further object to provide an anti-bacterial preventative agent for application to prevent the growth of bacteria, whether topically or internally.

DETAILED DESCRIPTION

Twenty-one Gram-positive and Gram-negative aerobic and anaerobic species of bacteria were selected. Each of the bacteria selected plays a well-known etiological role in causing various diseases. The bacteria used and the locus of human infection and the nature of the infection caused is set out below.

A. AEROBIC GRAM-POSITIVE COCCI

1. *Staphylococcus aureus:* (Family: Micrococcaceae; Genus: Staphylococcus): These are common inhabitants of the skin and mucous membranes and are etiological agents of a wide variety of human and animal infections including bacteremia, bacterial endocarditis, wound infections, and urinary tract infections.

2. *Streptococcus pyogens:* (Family Streptococcaceae; Genus: Streptococcus): Beta hemolytic Streptococcus Group A. This genus and species are found in the pharynx and cause upper respiratory tract infections.

3. *Streptococcus agalactiae:* (Family: Streptococcaceae; Genus: Streptococcus): Beta Hemolytic Streptococcus Group B: This species is found in the genital and intestinal tracts.

4. *Streptococcus pneumoniae:* (Family: Streptococcaceae: Genus: Streptococcus): Beta Hemolytic Streptococcus Group B: This bacteria is often found in patients with bacterial pneumonia.

5. *Streptococcus mutans* and 6. *Streptococcus sanguis:* (Family: Streptococcaceae; Genus: Streptococcus): Both are indicated as a primary cause of dental caries and are known to be primary causes of bacterial endocarditis.

B. AEROBIC GRAM-NEGATIVE BACTERIA

1. *Pseudomonas diminuta;* (2) *Pseudomonas vesicularis;* and (3) *Pseudomonas aeruginosa:* (Family: Pseudomonadaceae; Genus: Pseudomononas (Gram-negative rods)): These are often found in surgical wounds, ulcers, abscesses, burns, drainings, sinuses, ear infections, and lungs of patients treated with antibiotics. They can also cause severe diarrhea in infants and are a major cause in the death of burn patients.

4. *Pseudomonas maltophilia:* (Family: Pseudomonadaceae; Genus: Pseudomonas): This species has been associated with infections in humans including endocarditis, septicemia, lobar pneumonia, bronchopneumonia, urinary tract infections, conjunctivitis, actue mastoiditis, meningitis and wound infections.

5. *Neisseria sicca:* (Family: Neisseriaceae; Genus: Neisseria): This is found in the nasal pharynx and has been implicated as an etiological agent in the infections of meningitis, bacteremia, endocarditis, empyema and pneumonia.

C. ANAEROBIC GRAM-POSITIVE COCCI

1. *Peptococcus magnus:* (Family: Peptococcaceae; Genus: Peptococcus): This species inhabits the mouth and has been isolated from human infections in septic arthritis, Osteomyelitis, Bacteremia and is considered a significant cause of septic arthritis.

D. ANAEROBIC GRAM-NEGATIVE COCCI

1. *Veillonella parvula:* (Family: Veillonellaceae; Genus: Veillonella): This bacteria is found in the mouth, upper respiratory tract and large intestine.

E. GRAM-NEGATIVE NON-SPOREFORMING ANAEROBIC BACILLI (1) *Fusobacterium nucleatum:* (Family: Bacteroidaceae; Genus: Fusobacterium); (2) *Bacteroides fragilis:* (Family: Bacteroidaceae; Genus: Bacteroides); (3) *Leptotrichia buccalis:* (Family: Bacteroidaceae; Genus: Leptotrichia): These three species are found in the mouth, upper respiratory tract, intestinal tract and urogenital tract.

(4) *Bacteroides melaninogenicus:* (Family: Bacteroidaceae; Genus: Bacteroides); (5) *Bacteroides melaninogenicus intermedius:* (Subspecies of B. Melaninogenicus)

(6) *Bacteroides asaccharolyticus:* (Family: Bacteroidaceae; Genus: Bacteroides): These three species are found in the mouth.

F. GRAM-POSITIVE NON-SPOREFORMING ANAEROBIC BACILLI

1. *Actinomyces israelii:* (Order: Actinomycetales; Family: Actinomycetaceae; Genus: Actinomyces): This bacteria inhabits the mouth including tonsillar crypts and dental calculus, and causes human actinomycosis and infections in cattle.

The antibacterial activity of phenolphthalein was determined in relationship to the above 20 organisms. Generally to determine the bactericidal ability of phenolphthalein, the laboratory methodology utilized was to determine the minimal concentration (MIC) of phenolphthalein in a nutrient medium containing a particular species of bacteria, required to inhibit or prevent growth of that bacteria in its nutrient medium. These are generally referred to by those in the art of microbiology and bacteriology as "dilution susceptibility" tests and are used to determine the minimal concentration (MIC) of an antibacterial or antimicrobic which is required to inhibit or prevent the growth of a microorganism or bacteria. Four different concentrations of phenolphthalein were tested for each bacteria's susceptibility.

MATERIALS AND METHODS

Twenty species of bacteria were acquired from commercial laboratories. Once they were acquired, they were prepared for the MIC analysis. Each selected bacteria was incubated in its specific nutritive broth for at least twenty-four hours to develop a viable, pure, cell culture (inoculum). After approximately twenty-four hours of incubation, the cells were prepared and kept aseptic.

Minimal inhibitory concentration (MIC) is the lowest concentration of phenolpthalein in a solution without any visible growth of bacteria. A faint haziness or small clump of possible growth was regarded as indicative of bacterial growth and therefore a "positive" result. If there was no visible growth, this indicated that the phenolphthalein was a successful antibacterial at the concentration used, and therefore a "negative" result. Different concentrations of phenolpthalein were tested.

The inoculum for each organism was prepared by incubation in a broth nutrient culture of the organism for at least 24 hours. The nutrient broth used for each culture was that set out, hereafter, in Chart I. After incubation for 24 hours, each inoculum culture was adjusted to its turbidity standard which is one-half of its McFarland Barium Chloride standard. To make this adjustment requires a dilution of the inoculum with broth according to the dilution ratios set-out in Chart I. Each ratio is 1:100, except for staphylococcus aureus which is 1:200 ratio. Thus, after dilution, the inoculum is 0.5–1.0% of its previous concentration.

Four different concentrations of phenolphthalein were prepared in test solutions: 500 $\mu$g/ml (microgram per millileter) in 10% PEG, 250 $\mu$g/ml in 5% PEG, 125 $\mu$g/ml in 2.5% PEG, and 62.5 $\mu$g/ml in 1.25% PEG. In order to prepare enough phenolphthalein, a large source of test phenolphthalein antibacterial solution was prepared as follows. First, 100 milligrams of phenolpthalein was dissolved or suspended in 20 milliliters of polyethylene glycol 400 (PEG) (molecular weight 380–420) in a 100 millileter volumetric flask. After complete dissolution of phenolphthalein in the PEG solvent, the flask was filled q.s. with distilled water to make the total solution of 100 ml. volume. Then this phenolphthalein-PEG-water solution was filter sterilized. After this, the test solution had a concentration of 1000 micrograms of phenolphthalein per milliliter of solution of 20% PEG and water.

Next, three different controls were prepared for each bacteria: (a) a diluent control solution comprised of PEG in $H_2O$ and the bacteria and its broth; (b) a positive organism control comprised of bacteria in its nutritive broth; (c) a negative organism control comprised of only nutritive broth with no organism. All of this was done using sterile equipment, and all diluent control solutions were also filter sterilized after preparation. Each aliquot of the control solutions and the phenolphthalein test solution were prepared in triplicate.

In order to prepare the aliquot test solutions for each concentration of phenolphthalein and the three control solutions in triplicate, the following was done for each bacteria. Four millileters of the appropriate nutrient broth (as according to Chart I) *without* the test bacteria were added to approximately thirty sterile test tubes. Then 4 mls. of 1000 microgram/ml. ($\mu$g/ml). of phenolphthalein in 20% PEG aqueous solution as previously prepared were added to the first three test tubes which had 4 millileters of broth in each. This made a test solution with a concentration of 500 $\mu$g/ml. of phenolphthalein in 10% aqueous PEG in 8 mls. of test solution. In this same fashion of dilution, test solutions of 250 $\mu$g/ml. in 5% aqueous PEG, 125 $\mu$g/ml. in 2.5% aqueous PEG, and 62.5 $\mu$g/ml. in 1.25% aqueous PEG, were prepared for each bacteria in triplicate.

Next, to prepare the diluent controls for each concentration, 4 mls. of 20% PEG in $H_2O$ were first added to three test tubes which had 4 mls. of broth already, to make the first diluent control solution of 10% aqueous PEG. In this same dilution fashion, further diluent controls of 5% aqueous PEG, 2.5% aqueous PEG, and 1.25% aqueous PEG were prepared for each bacteria in triplicate.

Next, 0.1 milliliter of inoculum was added to *all* tubes at all concentrations *except* the negative organism control tubes. Thereafter all thirty tubes were incubated at the temperature specific for each bacteria (indicated on Chart I), for the time period also specific for each bacteria (indicated on Chart I). The results are set-out for each bacteria in the phenolphthalein test solution at the four different concentrations, the diluent controls at the four different concentrations, and the positive and negative organism controls. These results appear in Tables 1 through 21.

In reading and understanding these tables a positive (+) symbol indicates that growth was visually observed; a negative (−) symbol indicates that no growth was observed visually. The concentration figures used: 500 $\mu$g/ml, 250 $\mu$g/ml, 125 $\mu$g/ml, 62.5 $\mu$g/ml represent the test concentrations of phenolpthalein in aqueous 10%, 5%, 2.5%, 1.25% polyethylene glycol (PEG), respectively. The diluent control results are in the columns next to the phenolpthalein concentrations. They are 10% PEG, 5% PEG, 2.5% PEG, and 1.25% PEG respectively. At the right side of each table, the positive organism control and the negative organism control results are presented. The positive organism control is the control which is simply the test bacteria (inoculum) in its broth, incubated, without the addition of any further phenolphthalein or polyethylene glycol. The negative organism control is simply nutrient broth with no test bacteria (inoculum) added.

The results indicated in Tables 1 through 19 are summarized in Chart II below. In Chart II the interpretive symbols mean: (a) MIC means minimum inhibitory concentration of phenolphthalein; (b) LCT means lowest concentration of phenolpthalein tested; and (c) HCT means highest concentration of phenolpthalein tested.

Tests run against *Escherichia coli* and at the concentrations indicated by Table 20 were inconclusive at the concentrations used. Furthermore, tests run against the yeast *Candida albicans* showed that there was no inhibition in its growth at concentrations of 500 μg/ml. and less (Table 21). Tests at higher concentrations are presently being done.

These tests strongly indicate that under the conditions of the study that phenolphthalein prevents and inhibits bacterial growth in all species of the 20 organisms in some cases in concentrations as low as 62.5 μg/ml., and possibly in E. Coli at 500 μg/ml concentration. Further testing at higher concentrations might indicate whether phenolphthalein is effective against *Candida albicans*, and other yeasts.

Treatment of bacterially infected mammals or as a preventive measure against infection in mammals is believed to be accomplishable by application of phenolphthalein in therapeutic dosages. This can be done by application of phenolphthalein by itself, in a solution, or combined with carriers.

As will be readily appreciated by those in the art, phenolphthalein for oral application may be formulated with a variety of agents to treat or prevent those diseases, conditions and infections for which internal application is appropriate. The oral dosage may be administered in tablet, suspension, solution form or mouthwash form.

In preparing topical applications for the treatment or prevention of external diseases, conditions and infections, it is within the scope of the invention to formulate phenolphthalein with suitable carriers to aid in the application to or absorption into the target or affected area.

One group of carriers for external application, is the group including dimethyl sulfoxide (DMSO), petrolatum, mineral oil, and anhydrous lanolin. In most topical applications the concentration of the phenolphthalein in the carrier may vary widely.

In preparing the mixture of phenolphthalein and DMSO, one effective mixture is 150 milligrams phenolphthalein in 1 millileter DMSO. This concentration is not viewed as a lower limit as the maximum solubility of phenolphthalein in DMSO has not been determined. Another effective mixture requires mixing DMSO with phenolphthalein (already in aqueous solution), and then the further combination of this resulting solution with any suitable base cream, ointment or other carrier, such as lanolin or petrolatum.

Another carrier useful in external application is the mixture of methyl salicylate and lanolin, with phenolphthalein. Triethanolamine salicylate can be substituted for methyl salicylate. A mixture of polyethylene glycol as a carrier with phenolphthalein can also be used in external applications.

For external eyedrop applications the mixture of 0.1% phenolphthalein with the carrier solution of 1.4% polyvinyl alcohol, and 0.004% benzalkonium chloride as a preservative, with sodium chloride and edetate disodium as maintainers of the isotonicity of the solution can be used. Another solution for external eyedrop application can be prepared with phenyl mercuric nitrate, benzalkonium chloride, and boric acid as the carrier solution, with phenolphthalein in an effective dosage amount.

The above examples are not meant to be limiting, and the scope of the invention includes all effective concentrations of phenolphthalein in carriers. The invention is limited only by the scope of the claims set forth below.

CHART I

| | Bacteria | Nutrient Medium | Standard Turbidity Dilution Ratios | Incubation Temp. | Incubation Time |
|---|---|---|---|---|---|
| 1. | Staphylococcus Aureus | Nutrient broth | 1:200 | 37 C. | 24 hrs. |
| 2. | Streptococcus Pyogenes | Trypticase Soy Broth | 1:100 | 37 C. | 24 hrs. |
| 3. | Streptococcus Agalactiae | Trypticase Soy Broth | 1:100 | 37 C. | 24 hrs. |
| 4. | Streptococcus Pneumoniae | Trypticase Soy Broth | 1:100 | 37 C. | 24 hrs. |
| 5. | Streptococcus Mutans | Trypticase Soy Broth | 1:100 | 37 C. | 24 hrs. |
| 6. | Streptococcus Sanguis | Trypticase Soy Broth | 1:100 | 37 C. | 24 hrs. |
| 7. | Pseudomonas diminuta | Nutrient broth | 1:100 | 26 C. | 24 hrs. |
| 8. | Pseudomonas Vesicularis | Trypticase Soy Broth | 1:100 | 30 C. | 48 hrs. |
| 9. | Pseudomonas Aeruginosa | Trypticase Soy Broth | 1:100 | 30 C. | 48 hrs. |
| 10. | Pseudomonas Maltophilia | Trypticase Soy Broth | 1:100 | 30 C. | 48 hrs. |
| 11. | Mycoplasma Salivarium | Nutrient broth | 1:100 | 35 C. | 24 hrs. |
| 12. | Neisseria Sicca | Nutrient broth | 1:100 | 35 C. | 24 hrs. |
| 13. | Peptococcus Magnus | Nutrient Broth Containing a Supplemented Thioglycolate broth. BBL-0135C with 5 ug of Hemin per ml, and 5% Fildes extract | 1:100 | 35 C. | 5 Days |
| 14. | Veillonella Parvula | Nutrient Broth | 1:100 | 35 C. | 5 Days |

CHART I-continued

| | Bacteria | Nutrient Medium | Standard Turbidity Dilution Ratios | Incubation Temp. | Incubation Time |
|---|---|---|---|---|---|
| 15. | Fusobacterium nucleatum | Nutrient Broth Containing a Supplemented Thioglycolate broth. BBL-0135C with 5 ug of Hemin per ml, and 5% Fildes extract | 1:100 | 35 C. | 5 Days |
| 16. | Bacteroides Fragilis | Nutrient Broth Containing a Supplemented Thioglycolate broth. BBL-0135C with 5 ug of Hemin per ml, and 5% Fildes extract | 1:100 | 35 C. | 5 Days |
| 17. | Leptotrichia buccalis | Nutrient Broth Containing a Supplemented Thioglycolate broth. BBL-0135C with 5 ug of Hemin per ml, and 5% Fildes extract | 1:100 | 35 C. | 5 Days |
| 18. | Bacteroides Melaninogenicus | Nutrient Broth Containing a Supplemented Thioglycolate broth. BBL-0135C with 5 ug of Hemin per ml, and 5% Fildes extract | 1:100 | 35 C. | 7 Days |
| 19. | Bacteroides Melaninogenicus Intermedius | Nutrient Broth Containing a Supplemented Thioglycolate broth. BBL-0135C with 5 ug of Hemin per ml, and 5% Fildes extract | 1:100 | 35 C. | 7 Days |
| 20. | Bacteroides Asaccharolyticus | Nutrient Broth Containing a Supplemented Thioglycolate broth. BBL-0135C with 5 ug of Hemin per ml, and 5% Fildes extract | 1:100 | 35 C. | 7 Days |
| 21. | Actinomyces Israelii | Nutrient Broth Containing a Supplemented Thioglycolate broth. BBL-0135C with 5 ug of Hemin per ml, and 5% Fildes extract | 1:100 | 35 C. | 14 Days |

CHART II

| | BACTERIA | MIC | LCT | HCT |
|---|---|---|---|---|
| 1. | Staphylococcus Aureus | 125 ug/ml | 125 ug/ml | 500 ug/ml |
| 2. | Streptococcus Pyogenes | 125 ug/ml | 62.5 ug/ml | 500 ug/ml |
| 3. | Streptococcus Agalactiae | 125 ug/ml | 62.5 ug/ml | 500 ug/ml |
| 4. | Streptococcus Pneumoniae | 125 ug/ml | 62.5 ug/ml | 500 ug/ml |
| 5. | Streptococcus Mutans | 125 ug/ml | 62.5 ug/ml | 500 ug/ml |
| 6. | Streptococcus Sanguis | 125 ug/ml | 62.5 ug/ml | 500 ug/ml |
| 7. | Pseudomonas diminuta | 62.5 ug/ml | 62.5 ug/ml | 500 ug/ml |
| 8. | Pseudomonas Vesicularis | 62.5 ug/ml | 62.5 ug/ml | 500 ug/ml |
| 9. | Pseudomonas Aeruginosa | 62.5 ug/ml | 62.5 ug/ml | 500 ug/ml |

CHART II-continued

| | BACTERIA | MIC | LCT | HCT |
|---|---|---|---|---|
| 10. | Pseudomonas Maltophilia | 62.5 ug/ml | 62.5 ug/ml | 500 ug/ml |
| 11. | Mycoplasma Salivarium | 62.5 ug/ml | 62.5 ug/ml | 500 ug/ml |
| 12. | Neisseria Sicca | 62.5 ug/ml | 62.5 ug/ml | 500 ug/ml |
| 13. | Peptococcus Magnus | 125 ug/ml | 62.5 ug/ml | 500 ug/ml |
| 14. | Veillonella Parvula | 125 ug/ml | 62.5 ug/ml | 500 ug/ml |
| 15. | Fusobacterium nucleatum | 125 ug/ml | 62.5 ug/ml | 500 ug/ml |
| 16. | Bacteroides Fragilis | 125 ug/ml | 62.5 ug/ml | 500 ug/ml |
| 17. | Leptotrichia buccalis | 125 ug/ml | 62.5 ug/ml | 500 ug/ml |
| 18. | Bacteroides Melaninogenicus | 125 ug/ml | 62.5 ug/ml | 500 ug/ml |
| 19. | Bacteroides Melaninogenicus Intermedius | 125 ug/ml | 62.5 ug/ml | 500 ug/ml |
| 20. | Bacteroides Asaccharolyticus | 125 ug/ml | 62.5 ug/ml | 500 ug/ml |
| 21. | Actinomyces Israelii | 125 ug/ml | 62.5 ug/ml | 500 ug/ml |

APPENDIX I

TABLE 1

Minimum Inhibitory Concentration
*Staphylococcus Aureus*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | + | − | + | − | + | | | + | − |
| 2 | − | + | − | + | − | + | | | + | − |
| 3 | − | | − | − | | | | | + | − |

TABLE 2

Minimum Inhibitory Concentration
*Streptococcus Pyogenes*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | + | − | + | − | + | − | + | + | − |
| 2 | − | + | − | + | − | + | + | + | + | − |
| 3 | − | + | − | + | − | + | − | + | | |

EXPLANATORY NOTE: ug/ml = micrograms per millileter

TABLE 3

Minimum Inhibitory Concentration
*Streptococcus Agalactiae*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | + | − | + | − | + | + | + | + | − |
| 2 | − | + | − | + | − | + | − | + | + | − |
| 3 | − | + | − | + | − | + | − | + | | |

TABLE 3½

Minimum Inhibitory Concentration
*Streptococcus Pneumoniae*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | + | − | + | − | + | − | + | + | − |
| 2 | − | + | − | + | − | + | − | + | + | − |
| 3 | − | + | − | + | − | + | + | + | | |

EXPLANATORY NOTE: ug/ml = micrograms per milliliter

TABLE 4

Minimum Inhibitory Concentration
*Streptococcus Mutans*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | + | − | + | − | + | − | + | + | − |
| 2 | − | + | − | + | − | + | + | + | + | − |
| 3 | − | + | − | + | − | + | − | + | | |

TABLE 5

Minimum Inhibitory Concentration
*Streptococcus Sanguis*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | + | − | + | − | + | + | + | + | − |
| 2 | − | + | − | + | − | + | − | + | + | − |
| 3 | − | + | − | + | − | + | − | + |   |   |

EXPLANATORY NOTE: ug/ml = micrograms per milliliter

TABLE 6

Minimum Inhibitory Concentration
*Pseudomonas diminuta*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | − | − | + | − | + | − | + | + | − |
| 2 | − | − | − | + | − | + | − | + | + | − |
| 3 | − | − | − | + | − | − | − | − |   |   |

TABLE 7

Minimum Inhibitory Concentration
*Pseudomonas Vesicularis*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | − | − | + | − | + | − | + | + | − |
| 2 | − | − | − | + | − | + | − | + | + | − |
| 3 | − | − | − | + | − | − | − | + | + | − |

EXPLANATORY NOTE: ug/ml = micrograms per milliliter

TABLE 8

Minimum Inhibitory Concentration
*Pseudomonas Aeruginosa*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | − | − | + | − | + | − | + | + | − |
| 2 | − | − | − | + | − | + | − | + | + | − |
| 3 | − | − | − | + | − | + | − | + | + | − |

TABLE 9

Minimum Inhibitory Concentration
*Pseudomonas Maltophilia*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | − | − | + | − | + | − | + | + | − |
| 2 | − | − | − | + | − | + | − | + | + | − |
| 3 | − | − | − | + | − | + | − | − |   |   |

EXPLANATORY NOTE: ug/ml = micrograms per milliliter

TABLE 10

Minimum Inhibitory Concentration
*Neisseria Sicca*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | − | − | + | − | + | − | + | + | − |
| 2 | − | − | − | + | − | + | − | + | + | − |
| 3 | − | − | − | + | − | − | − | + | + | − |

EXPLANATORY NOTE: ug/ml = micrograms per milliliter

TABLE 11

Minimum Inhibitory Concentration
*Peptococcus Magnus*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | + | − | + | − | + | − | + | + | − |
| 2 | − | + | − | + | − | + | + | + | + | − |

TABLE 11-continued

Minimum Inhibitory Concentration
*Peptococcus Magnus*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 3 | − | + | − | + | − | + | − | + | | |

TABLE 12

Minimum Inhibitory Concentration
*Veillonella Parvula*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | + | − | + | − | + | + | + | + | − |
| 2 | − | + | − | + | − | + | − | + | + | − |
| 3 | − | + | − | + | − | + | − | + | + | − |

EXPLANATORY NOTE: ug/ml = micrograms per milliliter

TABLE 13

Minimum Inhibitory Concentration
*Fusobacterium nucleatum*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | + | − | + | − | + | − | + | + | − |
| 2 | − | + | − | + | − | + | − | + | + | − |
| 3 | − | + | − | + | − | + | + | + | + | − |

TABLE 14

Minimum Inhibitory Concentration
*Bacteroides Fragilis*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | + | − | + | − | + | + | + | + | − |
| 2 | − | + | − | + | − | + | − | + | + | − |
| 3 | − | + | − | + | − | + | − | + | | |

EXPLANATORY NOTE: ug/ml = micrograms per milliliter

TABLE 15

Minimum Inhibitory Concentration
*Leptotrichia buccalis*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | + | − | + | − | + | − | + | + | − |
| 2 | − | + | − | + | − | + | + | + | + | − |
| 3 | − | + | − | + | − | + | − | + | + | − |

TABLE 16

Minimum Inhibitory Concentration
*Melaninogenicus subspecie* of
*B. Melaninogenicus-B Asaccharolyticus* Group

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | + | − | + | − | + | − | + | + | − |
| 2 | − | + | − | + | − | + | − | + | + | − |
| 3 | − | + | − | + | − | + | + | + | + | − |

EXPLANATORY NOTE: ug/ml = micrograms per milliliter

TABLE 17

Minimum Inhibitory Concentration
*Intermedius subspecie* of
*B. Melaninogenicus-B Asaccharolyticus* Group.

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | + | − | + | − | + | − | + | + | − |
| 2 | − | + | − | + | − | + | − | + | + | − |
| 3 | − | + | − | + | − | + | + | + | + | − |

TABLE 18

Minimum Inhibitory Concentration
*Asaccharolyticus* (full specie status)

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | + | − | + | − | + | + | + | + | − |
| 2 | − | + | − | + | − | + | − | + | + | − |
| 3 | − | + | − | + | − | + | − | + | + | − |

EXPLANATORY NOTE: ug/ml = micrograms per milliliter

TABLE 19

Minimum Inhibitory Concentration
*Actinomyces Israelii*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | + | − | + | − | + | − | + | + | − |
| 2 | − | + | − | + | − | + | + | + | + | − |
| 3 | − | + | − | + | − | + | − | + | | |

TABLE 20

Minimum Inhibitory Concentration
*Escherichia coli*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | − | − | + | + | + | + | / | / | + | − |
| 2 | − | − | + | + | + | + | / | / | + | − |
| 3 | − | − | + | | + | | / | / | + | − |

TABLE 21

Minimum Inhibitory Concentration
*Candida Albicans*

| Tube | 500 mg/ml | Control 10% PEG | 250 mg/ml | Control 5% PEG | 125 mg/ml | Control 2.5% PEG | 62.5 mg/ml | Control 1.25% PEG | Positive Control | Negative Control |
|---|---|---|---|---|---|---|---|---|---|---|
| 1 | + | + | + | + | + | + | + | + | + | − |
| 2 | + | + | + | + | + | + | + | + | + | − |
| 3 | + | + | + | + | + | + | + | + | | |

EXPLANATORY NOTE: ug/ml = micrograms per milliliter

It is claimed:

1. The method of treating the condition, disease, or symptom of an infection caused by bacteria in mammals comprising administering to a mammal in need of such treatment an antibacterially effective amount of 3, 3-Bis(p-hydroxyphenyl)phthalide.

2. The method of claim 1 wherein the bacteria is bacteria classified in the genera selected from the group consisting of staphylococcus, streptococcus, pseudomonas, neisseria, peptococcus, veillonella, bacteroides, fusobacterium, leptotrichia, actinomyces, and combinations thereof.

3. The method of claim 1 wherein the bacteria is bacteria classified in the family selected from the group consisting of micrococcaceae, streptococcaceae, pseudomonadaceae, neisseriaceae, peptococcaceae, veillonellaceae, bacteroidaceae, actinomycetaceae, and combinations thereof.

4. The method of claim 1 wherein the bacteria is bacteria classified in the species selected from the group consisting of *Staphylococcus aureus, Streptococcus pyogenes, Streptococcus agalactiae, Streptococcus Pneumoniae, Streptococcus mutans, Streptococcus sanguis, Pseudomonas diminuta, Pseudomonas vesicularis, Pseudomonas aeruginosa, Pseudomonas maltophilia, neisseria sicca, Peptococcus magnus, Veillonella parvula, Fusobacterium nucleatum, Bacteroides fragilis, Leptotrichia buccalis, Bacteroides melaninogenicus, Bacteroides melaninogenicus intermedius, Bacteroides asaccharolyticus, Actinomyces israelii*, and combinations thereof.

5. The method of claim 1, wherein the condition, disease, symptom or infection is an infection of the mucous membrane, bacteremia, bacterial endocarditis, wound infection, urinary tract infections, upper respiratory tract infections, infections in the genitalia and intestinal tract, bacterial pneumonia, dental caries, infections in surgical wounds, ulcers, abscesses, burns, draining sinuses, ear infections, and lungs of mammals treated with antibiotics, diarrhea, septicemia, lobar pneumonia, bronchopneumonia, conjunctivitis, acute mastoiditis, meningitis, empyema, septic arthritis, osteomyelitis, and infections of the mouth, intestinal tract or urogenital tract.

6. The method of claim 1, 2, 3, 4 or 5 wherein the 3, 3-Bis(p-hydroxyphenyl)phthalide is dissolved or suspended in in a pharmaceutically acceptable liquid.

7. The method of claim 1, 2, 3, 4 or 5 wherein 3, 3-Bis(p-hydroxyphenyl)phthalide is suspended or dissolved in a pharmaceutically acceptable liquid in an amount of at least about sixty-two micrograms per milliliter of the liquid.

8. The method of claim 1, 2, 3, 4 or 5 wherein 3, 3-Bis(p-hydroxyphenyl)phthalide is suspended or dissolved in a pharmaceutically acceptable liquid in an amount of at least about one hundred and twenty-five micrograms per milliliter of the liquid.

9. The method of claim 1, 2, 3, 4 or 5 wherein 3, 3-Bis(p-hydroxyphenyl)phthalide is suspended or dissolved in a pharmaceutically acceptable liquid in an amount of at least about two hundred and fifty micrograms per milliliter of the liquid.

10. The method of claim 1, 2, 3, 4 or 5 wherein 3, 3-Bis(p-hydroxyphynyl)phthalide is suspended or dissolved in a pharmaceutically acceptable liquid in an amount of at least about five hundred micrograms per milliliter of the liquid.

11. The method of claim 1, 2, 3, 4 or 5 wherein the mammal is a human.

12. The method of claim 6 wherein water is the pharmaceutically acceptable liquid.

13. The method of claim 1, 2, 3, 4 or 5 wherein the 3, 3-Bis(p-hydroxyphenyl)phthalide is disbursed in a topical carrier.

14. The method of claim 13 wherein the topical carrier is dimethyl sulfoxide.

* * * * *